United States Patent [19]

Gosciniak et al.

[11] Patent Number: 4,891,212

[45] Date of Patent: Jan. 2, 1990

[54] ULTRAVIOLET RADIATION ABSORBING CYCLOHEXENYLIDENE CYANOACETATE ESTER AND AMIDE COMPOSITIONS

[75] Inventors: Donald J. Gosciniak, West Chester, Pa.; Thomas P. Cleary; Charlambos J. Phalangas, both of Wilmington, Del.

[73] Assignee: ICI Americas Inc., Wilmington, Del.

[21] Appl. No.: 290,800

[22] Filed: Dec. 28, 1988

[51] Int. Cl.[4] .................. A61K 31/275; C07C 121/48; C07C 121/52

[52] U.S. Cl. .................................. 424/59; 558/404; 558/406; 558/430

[58] Field of Search .................. 424/59; 558/404, 406, 558/430

[56] References Cited

PUBLICATIONS

Chem. Abstracts, vol. 95, No. 8; Abst. No. 96829 n to Bardakos et al, (1981).

*Primary Examiner*—Joseph Paul Brust
*Assistant Examiner*—Mary Sue Howard
*Attorney, Agent, or Firm*—William E. Dickheiser

[57] ABSTRACT

Sunscreen compositions are described which contain certain cyclohexenylidene cyanoacetate esters and amides which act as UV filters when incorporated in a carrier in amounts ranging from 0.1–50% by weight.

14 Claims, No Drawings

ULTRAVIOLET RADIATION ABSORBING CYCLOHEXENYLIDENE CYANOACETATE ESTER AND AMIDE COMPOSITIONS

The present invention is directed to ultraviolet absorbing compositions comprising substituted cyclohexenylidene cyanoacetate esters and amides and blends thereof which are useful as protective coatings and to a method for protecting substrates against the harmful effects of actinic radiation. It is further directed to a process for making ultraviolet absorbing coating compositions.

Ultraviolet radiation absorbing coatings are useful in protecting substrates such as plastics against accelerated deterioration and the skin of warm blooded animals against severe erythema, edema and blistering when exposed to sunlight. The cyanoacetate compositions of this invention are generally referred to as sunscreen compositions and blends thereof can be incorporated with waxes, oils, lacquers and soft resins in the preparation of furniture and auto polishes, as well as cosmetics, suntan oils, lotions, lipstick, hair treatments, skin formulations and in addition can be incorporated with contact lenses.

This invention relates to sunscreen compositions comprising a carrier having incorporated therein an effective amount of a ultraviolet absorber selected from a compound of general Formula I:

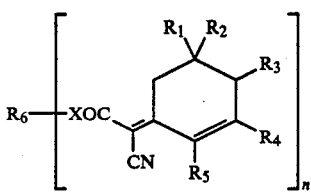

wherein
X is selected from O or NH and $R_1$–$R_5$ are selected from H or alkyl groups having 1-5 carbon atoms;
n is 2 or 3; but when
n=2, $R_6$ is selected from divalent alkylene groups of 2-16 carbon atoms, cycloalkylene groups of 5-8 carbon atoms, arylene groups of 6-12 carbon atoms or alkylarylene groups of 7-13 carbon atoms, and when
n=3, $R_6$ is selected from trivalent alkylene groups of 3-16 carbon atoms.

Preferred compounds are those wherein X is O, $R_6$ is selected from alkylene groups of 3-12 carbon atoms and n is 2.

The method for protecting substrates comprise topically applying the compound of formula I in an acceptable carrier. Of particular interest are compounds which provide selective absorption of UV radiation in the 290-320 nm as well as the 320-400 nm range of wavelengths. The compounds may be dissolved in the coating compositions or present as a finely divided solid or as a solid dispersed in an acceptable carrier. The selection of carrier used in the coating composition must not interfere with the absorption in the 290-400 nm range.

The compositions of the invention comprise UV filter compounds of Formula I in amounts needed to provide desired protection against the harmful effects of ultraviolet radiation. The concentration of the compounds in the composition is regulated such that when the composition is topically applied, the desired protection is provided. The amount needed to provide the desired protection can vary with the characteristics of the compound, that is, its extinction coefficient, substantivity, the nature of the carrier, the source and intensity of the radiation and other well recognized variables. Suitable amounts can be readily determined by standard methods of testing. Preferably UV filter compounds are incorporated in an amount ranging from about 0.1 percent to about 50 percent by weight and usually in amounts of 1.0-30 percent by weight and preferred amounts ranging from 1.5-15 percent by weight based on the total weight of the coating composition.

Acceptable carriers include any vehicle or medium capable of incorporating the UV filter compound in a manner permitting uniform topical application. The term "pharmaceutically acceptable" is intended as a qualifier when the carrier is dermatologically innocuous to warm blooded animals and cosmetically acceptable. However all carriers are not useful on skin. The carrier may comprise a wax, oil or cream base material in which the agent can be held in a clear solution or a uniform dispersion for example as submicron sized particles. Preferably the carrier comprises a suitable solvent or a mixture of solvents capable of dissolving the UV filter compounds to provide a concentration that is effective as a filtering agent when incorporated in the sunscreen formulation. Solvents which may be useful include alcohols, ketones, esters, polyol esters, oils, hydrocarbons, chlorinated hydrocarbons, ethers, polyethers, polyetherpolyols and other special solvents such as dimethylsulfoxide, dimethylformamide, dimethylisosorbide, isopropylmyristate and the like. Such solvents are considered useful only if they do not permanently interact with the active UV filtering compound of the invention to shift the total effective absorption outside the 290-400 nm range. Some of the above named ingredients are not pharmaceutically acceptable but are useful in other applications.

The invention is directed to a method for protecting a substrate against the effects of ultraviolet radiation which comprises topically applying the above described compounds in a carrier.

The sunscreening compositions may be applied as a clear liquid or a lotion comprising a water-in-oil, oil-in-water or a multiple emulsion. Either the oil or water base or both may be used as a carrier for the sunscreening composition. The oil base material and the water and oil base compositions will form a continuous film of the UV filtering compound. Such films also provide long lasting protection against sun induced erythema. Sunscreening formulations are generally used in hot weather and at beaches where people enjoy bathing activity. It is also essential that the protective coating applied to the skin is not appreciably affected by water or perspiration. The pharmaceutically acceptable compositions herein disclosed are included in a thin layer protective coating on the skin of warm blooded animals and provide long lasting protection against erythema and do not appreciable decompose over practical periods of exposure to sunlight.

The starting cyclohexenylidenes are conveniently made by condensing cyanoacetate esters with an appropriate cyclohexenyl ketone in the presence of a catalyst as described in Org. Mag. Res., 15, 339 (1981) and J. Chem. Soc., 1570 (1926). These cyclohexenylidene esters are then condensed with di- or trihydroxy or amine compounds of 2-16 carbon atoms using acid or base catalyst. The cyclohexenyl ketones are commercially available or can be synthesized by condensing 3-oxoesters with a Mannich base in the presence of an acid catalyst as described in Can. J. Chem., 56, 1646 (1978) and U.S. Pat. No. 4,418,087.

The following preparative examples serve as nonlimiting illustrations of the type of compounds included in the invention and all parts and percentages are expressed on a weight basis unless otherwise specified.

Preparation 1

In a 50 ml 3-necked round bottom flask equipped with a reflux condenser and a nitrogen inlet were placed methyl 2(3,5,5-trimethyl-2-cyclohexenylidene)cyanoacetate (5.0 g, 0.023 mol), 2,2-dimethyl-1,3-propaneidol (0.9 g, 0.0115 mol) and cyclohexane (20 g, 0.23 mol). The mixture was heated to 80° C. and the lithium amide (0.3 g, 0.0013 mol) added all at once. The reaction was refluxed with azeotropic removal of methanol for 2.0 hours. The reaction was then quenched with acetic acid (0.5 ml), ethanol (20 ml) added, and cooled to 0° C. The precipitated product was then filtered washed with hexane and dried. The off-white solid has a λmax=306 nm and a K value=98.

Preparation 2

This material was prepared according to the procedure for preparation 1 wherein 1,12-dodecanediol was substituted for 2,2-dimethyl-1,3-propanediol. The product was isolated as an oil and has a λmax=305 nm and a K value=80.

Preparation 3.

This material could be prepared according to the procedure for preparation 1 wherein 1,6-hexanediamine is substituted for 2,2-dimethyl-1,3-propanediol.

Preparation 4

This material could be prepared according to the procedure for preparation 1 wherein 4-hydroxybenzyl alcohol is substituted for 2,2-dimethyl-1,3-propanediol.

Preparation 5

This material could be prepared according to the procedure for preparation 1 wherein 1,1,1-tris(hydroxymethyl)ethane is substituted for 2,2-dimethyl-1,3-propanediol.

Preparation 6

This material could be prepared according to the procedure for preparation 1 wherein 4,4'-biphenol is substituted for 2,2-dimethyl-1,3-propanediol.

UV-B (290–320 nm) and the tanning range UV-A (320–400 nm). Since approximately 76% of the physiological tanning potential of sunlight is found in the UV-B range and the balance is found in the UV-A range, it is desirable to have a substantial amount of the radiation in those ranges filtered out before it produces a harmful effect on the surface of human skin. While sunscreen lotions have been formulated to be most effective in the UV-B range recent studies have indicated that it is desirable to have collective adsorption in the UV-A range as well. It has been difficult to find a practical compound which effectively absorbs in both ranges. Therefore, formulators must restort to the combination of two compounds which are each effective either in the UV-B, or UV-A range to provide maximum skin protection. No single compound falling within the definition of formula I is effective over the entire 290–400 nm range and therefore two or more compounds can be selected and blended within the formulation at varying concentrations until the desired balance between burning and tanning is accommodated. Such combinations are shown in Examples 8, 9 and 11. It is preferred to have a formulation having at least one compound which absorbs in the 290–320 nm range and at least one other which absorbs in the 320–400 nm range. At least one is selected from Formula I.

The use of the UV filters of the invention can be demonstrated in lotion formulations which are topically applied to the surface of the skin. The effectiveness of the UV light absorbers are tested on human subjects by treating a 1 cm square section of a subjects' back with predetermined amounts of lotion, exposing the treated areas to UV light for a period of time and thereafter making a visual comparison with untreated and fully masked skin areas. The SPF (skin protection factor) is calculated by comparing the effects of radiation on protected skin with the unprotected skin.

Besides the SPF determinations on humans, many in vitro methods and in vivo tests on animal models are also widely used. Some of these methods yield results which correlate well with SPF determined on humans and are useful tools for evaluating new compounds.

The following lotions and creams will serve to illustrate but not limit those which can be used in the practice of the invention.

In general, typical formulating techniques are well known to skilled formulators and usually require that the filtering agent be first added to the oil phase which is thereafter emulsified. With regards to examples 1–10 and controls, all ingredients can be mixed together and stirred in conventional apparatus. Since in many cases a single compound used at a reasonable concentration

| EXAMPLES OF UV ABSORBING ESTERS AND AMIDES | | | | | | | | |
|---|---|---|---|---|---|---|---|---|
| Prep | n | X | $R_1$ | $R_2$ | $R_3$ | $R_4$ | $R_5$ | $R_6$ |
| 1 | 2 | —O— | $CH_3$ | $CH_3$ | H | $CH_3$ | H | $-CH_2C(CH_3)_2CH_2-$ |
| 2 | 2 | —O— | $CH_3$ | $CH_3$ | H | $CH_3$ | H | $-CH_2(CH_2)_{10}CH_2-$ |
| 3 | 2 | —O— | $CH_3$ | $CH_3$ | H | $CH_3$ | H | $-C_6H_4-C_6H_4-$ |
| 4 | 2 | —NH— | $CH_3$ | $CH_3$ | H | $CH_3$ | H | $-CH_2(CH_2)_4CH_2-$ |
| 5 | 2 | —O— | $CH_3$ | $CH_3$ | H | $CH_3$ | H | $-C_6H_4CH_2-$ |
| 6 | 3 | —O— | $CH_3$ | $CH_3$ | H | $CH_3$ | H | $CH_3C(CH_2)_3-$ |

It has been established that actinic radiation between 290 nm and 320 nm produces substantially all the burning or erythemal energy and a substantial portion of the tanning energy, while the radiation between 320 nm and 400 nm produces incident tanning. The cosmetic industry has divided these spectra into the burning range does not effectively protect throughout the whole region of the earth reaching solar UV spectrum, blends of two or more UV absorbers can be used in a formulation to afford greater protection.

To illustrate the effectiveness of the compounds of the invention in sunscreen application oligomer compounds of Preparations 1 and 2 were formulated into creams and lotions for testing. The formulations of Examples 1-10 are shown in Table 1.

EXAMPLES 1-10

Blending Procedure for Examples 1, 2, 5-8:

Heat mixed ingredients of (A) to 70° C. Heat mixture B to 75° C. then add to (A). Add (C).

Examples 3, 4, 9 and 10 are clear solutions of (E).

TABLE 1

SUNSCREEN FORMULATIONS

| Ingredient | 1 | 2 | 3 | 4 | 5 | 6 | 7 | 8 | 9 | 10 |
|---|---|---|---|---|---|---|---|---|---|---|
| Preparation No. 1 | 8 | 3 | 8 | 3 | — | — | — | — | — | — |
| Preparation No. 2 | — | — | — | — | 8 | 8 | 3 | 8 | 8 | 3 |
| Mineral Oil | 5 | 5 | — | — | 5 | 5 | 5 | 5 | — | 0 |
| Stearyl Alcohol | .5 | .5 | — | — | .5 | .5 | .5 | .5 | 0 | — |
| 21 Dendro Stearoyl-ether (Brij 721 ICI Americas) | 2.5 | 2.5 | — | — | 2 | 1.5 | 1.5 | 2.6 | — | — |
| 21 Dendro Stearoyl-ether (Brij 721 ICI Americas) | 1.5 | 1.5 | — | — | 2 | 2.5 | 2.5 | 1.4 | — | — |
| Silicone Oil SF96 (GE) | .5 | .5 | — | — | .5 | .5 | .5 | .5 | — | — |
| Cetyl Alcohol | .5 | .5 | — | — | — | .5 | .5 | — | — | — |
| (B) Water | 70.95 | 75.95 | — | — | 71.45 | 70.95 | 75.95 | 71.45 | — | — |
| Carbopol 934 2% sln. | 10 | 10 | — | — | 10 | 10 | 10 | 10 | — | — |
| (C) Sodium Hydroxide (10% aqueous) | .2 | .2 | — | — | .2 | .2 | .2 | .2 | — | — |
| (D) DMDMH-55 (Glyco) | .35 | .35 | — | — | .35 | .35 | .35 | .35 | — | — |
| (E) Dimethylisosorbide (Atlas G100) | — | — | 92 | 97 | — | — | — | — | 92 | 97 |
| Physical Form | | | | | | | | | | |
| Emulsion | X | X | | | X | X | X | X | | |
| Solution | | | X | X | | | | | X | X |

SUNSCREEN FORMULA

| Ingredient | 1 | 2 | Control D |
|---|---|---|---|
| Compound No.2 | 2 | 8 | 0 |
| Petrolatum (Snow White USP) | 35 | 35 | 35 |
| Polyoxyethylene (21) stearoyl ether | 1.16 | 1.16 | 1.16 |
| Polyoxyethylene (2) stearoyl ether | 3.86 | 3.86 | 3.86 |
| Silicone Oil | 3 | 3 | 3 |
| Water (deionized) | 54.08 | 48.08 | 56.08 |
| Carbopol ® 934 | 0.4 | 0.4 | 0.4 |
| Sodium Hydroxide (10%) | 0.4 | 0.4 | 0.4 |
| Dowicil ® 200 | 0.1 | 0.1 | 0.1 |
| Physical Form | cream | cream | cream |

Additional tests on female subjects ranging from ages 27-50 having skin type I (always burns easily, never tans), type II (always burns easily, tans minimally) and type III (burns moderately, tans gradually) are performed. Each subject is exposed to UV radiation on 3 separate days at 27, 28 and 29 (mW/cm$^2$) respectively. Templates are applied to individual skin sites on designated areas of the back. Application of the test material are made by uniformly spreading the lotion or cream over a 50 cm$^2$ area (3.5 cm by 14.3 cm) at a dose of 2 mg/cm$^2$ with a finger cot. Approximately 15 minutes after application the sites were irradiated. Test sites are scored approximately 24 hours after exposure.

In addition to their use in coating skin surfaces to prevent sunburn the compositions of the invention can also be employed in various formulations such as waxes, oils, lacquers and soft resins in the preparation of furniture and auto polishes, cosmetics, lipstick, hair treatments, skin formulations and contact lenses. The compounds of the invention act as filtering agents and may be used singly or in combination to provide a wider range of protection. The following formulations are given to demonstrate a few of the many applications.

| Example No. | Filtering Agent | Carrier Ingredients | Composition (% by Wt) |
|---|---|---|---|
| 3 | Aerosol Hairdressing | | |
| | Prep 1 | | 5.0 |
| | | Decaglycerol monolaurate | 2.0 |
| | | Polypropylene (200) monooleate | 3.0 |
| | | Ethoxylated (10) lanolin alcohols | 1.0 |
| | | Propylene glycol | 2.0 |
| | | Ethyl alcohol, anhydrous | 39.5 |
| | | Protein polypeptide (20% alcoholic) | 1.2 |
| | | Isopropyl myristate | 1.3 |
| | | Propellant 11 | 15.0 |
| | | Propellant 12 | 30.0 |
| | | Water | q.s. |
| | Procedure for Formula: Dissolve all ingredients in slightly warmed ethyl alcohol, avoiding loss of the alcohol, add the water, and agitate well to disperse any haze. Filter the concentrate and fill into aerosol containers. Add propellants. | | |
| 4 | Formula for Creamy Type Lipstick Base | | |
| | Prep 1 | | 5 |
| | | Carnauba wax | 3 |

-continued

| Example No. | Filtering Agent | Carrier Ingredients | Composition (% by Wt) |
|---|---|---|---|
| | | Candelilla wax | 7 |
| | | Ozokerite ® | 3 |
| | | Beeswax | 7 |
| | | Lanolin | 10 |
| | | Castor oil | 60 |
| | | Isopropyl myristate | 5 |
| | | Perfume | q.s. |
| 5 | Water-In-Oil (W/O), Detergent Resistant, Liquid Auto Polish | | |
| | Part A | 2.00% Durmont 500 Montan Wax | (Dura Commodities) |
| | Part B | 0.75% DC 530 Silicone Fluid | (Dow Corning) |
| | | 4.25% DC 531 ® Silicone Fluid | |
| | | 1.50% SPAN ® 80 (ICI Americas) sorbitan monooleate | |
| | | 10.00% Kerosene | |
| | | 16.50% Stoddard Solvent | |
| | | 5.0% Preparation 5 | |
| | Part C | 10.00% Kaopolite SFO | (Kaopolite) |
| | Part D | 50.00% Water | |
| | Method of Preparation: | | |
| | 1. Melt wax in Part A (85–90° C.) | | |
| | 2. Add Part B ingredients to melted wax and stir to blend well. Return temperature to 85–90° C. | | |
| | 3. Add Part C to Part A/Part B blend and mix until uniform with medium agitation Keep temperature in the 85–90° C. range | | |
| | 4. Heat Part D to 95° C. and slowly add to the blend with high speed stirring until emulsion is obtained. | | |
| | 5. Cool to 40–45° C. with continuous stirring. | | |
| | 6. Homogenize. | | |
| 6 | Neutral Base Lacquer | | |
| | Materials | | Pounds |
| | Urethane 60% N.V. | | 32 |
| | Long oil alkyd 60% N.V. | | 352 |
| | Triton X-45 | | 7.5 |
| | Nuxtra ® Calcium 6% | | 12 |
| | Bentone Jell 8% | | 28 |
| | Disperse the bentone jell under high speed cowles and add: | | |
| | Preparation 1 | | 16 |
| | Low odor mineral spirits | | 85 |
| | Cyclodex cobalt 6% | | 3 |
| | JK 270-70% | | 76 |
| | Water | | 205 |
| | Anti skin | | 2 |
| | Viscosity: | 80–85 KU | |
| | W/G: | 7.84 | |
| | 60° Gloss: | 85 | |
| | SAG: | 6 ml | |
| 7 | O/W Paraffin Wax Emulsion | | |
| | Part A | 50% Paraffin wax | |
| | | 5% SPAN 60/TWEEN 60 (50/50) (ICI Americas) (sorbitan monostearate/20 dendro sorbitan monostearate) | |
| | | 5% Preparation 6 | |
| | Part B | 40% Water | |
| | Method of Preparation: | | |
| | 1. Melt Part A ingredients together and heat to 80° C. | | |
| | 2. Heat Part B to 85° C. | | |
| | 3. Add Part B to Part A slowly with moderate agitation until inversion occurs. Add remaining water rapidly. | | |
| | 4. Cool in cold water bath with slow agitation to approximately 35° C. | | |

-continued

| Example No. | Filtering Agent | Carrier Ingredients | Composition (% by Wt) |
|---|---|---|---|
| 8 | O/W Soft Microcrystalline Wax Emulsion | | |
| | Part A | 30% Microcrystalline wax (Ultraflex Amber Wax-Petrolite Corp.) | |
| | | 30% SPAN ® 60/TWEEN ® 60 (78/22) | |
| | | 2.5% Preparation 2 | |
| | | 2.5% Preparation 6 | |
| | Part B | 62% Water | |
| | Method of Preparation: | | |
| | 1. Melt together Part A ingredients and heat to 80–90° C. | | |
| | 2. Heat Part B to boiling. | | |
| | 3. Add Part B to Part A slowly with moderate agitation until inversion occurs. Add remaining water rapidly. | | |
| | 4. Remove from heat and cool to room temperature without stirring. | | |
| 9 | O/W Carnauba Wax Emulsion | | |
| | Part A | 10% Carnauba wax | |
| | | 3% TWEEN 80 (ICI Americas) (20 dendro sorbitan monooleate) | |
| | | 2.5% Preparation 3 | |
| | | 2.5% Preparation 4 | |
| | Part B | 82% Water | |
| | Method of Preparation: | | |
| | 1. Melt Part A ingredients together and heat to 95° C. and hold. | | |
| | 2. Heat Part B to boiling. | | |
| | 3. Add Part B to Part A slowly with moderately fast stirring until inversion occurs. Add remaining water rapidly. | | |
| | 4. Remove emulsion from heat and cool rapidly with stirring. | | |

SUNSCREEN LOTION

EXAMPLE 10

| PHASE | INGREDIENTS (SUPPLIERS) | PERCENT BY WEIGHT |
|---|---|---|
| A | Petrolatum, Snow White USP (Ruger) | 35.00 |
| | Brij ® 721 (ICI Americas surfactant) | 1.16 |
| | BRij 72 (ICI Americas surfactant) | 3.86 |
| | Silicone Oil, 350 cs (Ruger) | 3.00 |
| | Preparation 1 | 5.00 |
| | Uvinul M-40 (BASF) | 3.00 |
| B | Water | 48.08 |
| | Carbopol ® 934 (B. F. Goodrich) | 0.40 |
| C | Sodium Hydroxide (10% Aqueous Solution) | 0.40 |
| D | Dowicil ® 200 (DOW) | 0.10 |

Preparation: Heat (A) to 60° C. Heat (B) to 65° C. Add (B) to (A) slowly with moderate agitation. Add (C). Cool to 50° C. Add (D). Cool, while stirring to 35° C.

SUNSCREEN LOTION

EXAMPLE 11

| PHASE | INGREDIENTS (SUPPLIERS) | PERCENT BY WEIGHT |
|---|---|---|
| A | Arlamol ® E (ICI Americas, 30 dendro stearyl alcohol) | 7.00 |
| | Stearyl Alcohol | 2.50 |
| | Silicone Oil, 350 cs (Ruger) | 5.00 |
| | Arlasolve 200 (ICI) | 2.10 |

| PHASE | INGREDIENTS (SUPPLIERS) | PERCENT BY WEIGHT |
|---|---|---|
| | Brij 72 (ICI) | 4.90 |
| | Preparation No 1 | 5.00 |
| | Preparation No 2 | 3.00 |
| B | Water | 70.00 |
| | Carbopol 934 (B. F. Goodrich) | 0.20 |
| C | Sodium Hydroxide (10% Aqueous Solution) | 0.20 |
| D | Dowicil 200 (DOW) | 0.10 |
| Preparation: | Heat (A) to 65° C. Heat (B) to 70° C. Add (B) to (A) slowly with moderate agitation. Add (C). Cool to 50° C. Add (D). Cool, while stirring to 35° C. | |

SUNSCREEN LOTION

EXAMPLE 12

| PHASE | INGREDIENTS (SUPPLIERS) | PERCENT BY WEIGHT |
|---|---|---|
| A | Arlamol E (ICI) | 7.00 |
| | Stearyl Alcohol | 2.50 |
| | Silicone Oil, 350 cs (Ruger) | 5.00 |
| | Arlasolve ® 200 (ICI 20 dendro isohexadecyl alcohol) | 2.10 |
| | Brij 72 (ICI) | 4.90 |
| | Preparation 5 | 8.00 |
| B | Water | 70.00 |
| | Carbopol ® 934 (B. F. Goodrich) | 0.20 |
| C | Sodium Hydroxide (10% Aqueous Solution) | 0.20 |
| D | Dowicil 200 (DOW) | 0.10 |
| Preparation: | Heat (A) to 60° C. Heat (B) to 65° C. Add (B) to (A) slowly with moderate agitation. Add (C). Cool to 50° C. Add (D). Cool, while stirring to 35° C. | |

SUNSCREEN LOTION

EXAMPLE 13

| PHASE | INGREDIENTS (SUPPLIERS) | PERCENT BY WEIGHT |
|---|---|---|
| A | Petrolatum, Snow White USP (Ruger) | 35.00 |
| | Brij 721 (ICI) | 1.16 |
| | Brij 72 (ICI) | 3.86 |
| | Preparation 1 | 8.00 |
| | Silicone Oil, 350 cs (Ruger) | 3.00 |
| B | Water | 49.08 |
| | Carbopol 934 (B. F. Goodrich) | 0.40 |
| C | Sodium Hydroxide (10% Aqueous Solution) | 0.40 |
| D | Dowicil 200 (DOW) | 0.10 |
| Preparation: | Heat (A) to 60° C. Heat (B) to 65° C. Add (B) to (A) slowly with moderate agitation. Add (C). Cool to 50° C. Add (D). Cool, while stirring to 35° C. | |

SUNSCREEN LOTION

EXAMPLE 14

Example 14

| PHASE | INGREDIENTS (SUPPLIERS) | PERCENT BY WEIGHT |
|---|---|---|
| A | Arlamol E (ICI) | 7.00 |
| | Stearyl Alcohol | 2.50 |
| | Silicone Oil, 350 cs (Ruger) | 5.00 |
| | Arlasolve ® 200 (ICI) | 2.10 |
| | Brij 72 (ICI) | 4.90 |
| | Preparation 4 | 5.50 |

Example 14-continued

| PHASE | INGREDIENTS (SUPPLIERS) | PERCENT BY WEIGHT |
|---|---|---|
| B | Water | 72.50 |
| | Carbopol 934 (B. F. Goodrich) | 0.20 |
| C | Sodium Hydroxide (10% Aqueous Solution) | 0.20 |
| D | Dowicil 200 (DOW) | 0.10 |
| Preparation: | Heat (A) to 65° C. Heat (B) to 70° C. Add (B) to (A) slowly with moderate agitation. Add (C). Cool to 50° C. Add (D). Cool, while stirring to 35° C. | |

What is claimed is:

1. A method for protecting a substrate against the effects of ultraviolet radiation by topically applying a composition comprising a carrier having incorporated therein an ultraviolet radiation protecting effective amount of a compound having the Formula I:

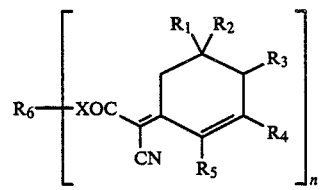

wherein
X is selected from O or NH and $R_1$–$R_5$ are selected from H or alkyl groups having 1–5 carbon atoms;
n is 2 or 3; but when
n=2, $R_6$ is selected from divalent alkylene groups of 2–16 carbon atoms, cycloalkylene groups of 5–8 carbons atoms, arylene groups of 6–12 carbon atoms or alkylarylene groups of 7–13 carbon atoms, and when
n=3, $R_6$ is selected from trivalent alkylene groups of 3–16 carbon atoms.

2. A method of claim 1 wherein said compound is incorporated in said composition in an amount ranging from about 0.1 to about 50% by weight.

3. A method of claim 2 wherein said compound is incorporated in said composition in an amount ranging from about 1 to about 15% by weight.

4. A method of claim 1 wherein said compound is dissolved in said carrier.

5. A method of claim 1 wherein said carrier is an aqueous emulsion.

6. A method of claim 1 wherein said substrate is the skin of a warm blooded animal.

7. A sunscreen composition comprising a pharmaceutically acceptable carrier containing 0.5–30% by weight of a compound selected from Formula I

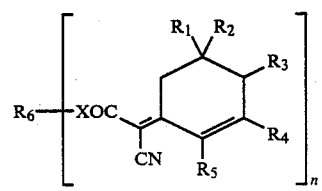

wherein
X is selected from O or NH and $R_1$–$R_5$ are selected from H or alkyl groups having 1–5 carbon atoms,
n is 2 or 3; but when n=2, $R_6$ is selected from divalent alkylene groups of 2–16 carbon atoms, cycloalkylene groups of 5–8 carbons atoms, arylene groups of 6–12 carbon atoms or alkylarylene groups of 7–13 carbon atoms, and when n=3, $R_6$ is selected from trivalent alkylene groups of 3–16 carbon atoms.

8. A composition of claim 7 having at least one compound selected from Formula I and at least one other compound which absorbs radiation in the 290–400 nm range.

9. A compound having the Formula I

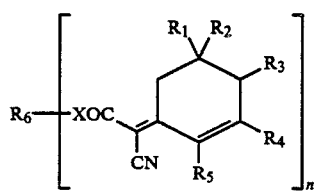

wherein
X is selected from O or NH and $R_1$–$R_5$ are selected from H or alkyl groups having 1–5 carbon atoms;
n is 2 or 3; but when
n=2, $R_6$ is selected from divalent alkylene groups of 2–16 carbon atoms, cycloalkylene groups of 5–8 carbons atoms, arylene groups of 6–12 carbon atoms or alkylarylene groups of 7–13 carbon atoms, and when n=3, $R_6$ is selected from trivalent alkylene groups of 3–16 carbon atoms.

10. Compounds of claim 9 wherein X is O, $R_6$ is selected from alkylene groups of 2–12 carbon atoms, and n is 2.

11. Compound of claim 9 wherein X is O, $R_6$ is n-butylene, and n is 2.

12. Compound of claim 9 wherein X is O, $R_6$ is 2,2-dimethyl-1,3-propylene, and n is 2.

13. Compound of claim 9 wherein X is O, $R_6$ is n-octylene, and n is 2.

14. Compound of claim 9 wherein X is O, $R_6$ is n-dodecylene, and n is 2.

* * * * *